US012778746B2

(12) United States Patent
Packer et al.

(10) Patent No.: US 12,778,746 B2
(45) Date of Patent: Nov. 3, 2026

(54) PROSTHETIC VENOUS VALVE DEVICES AND ASSOCIATED METHODS

(71) Applicant: Brigham Young University, Provo, UT (US)

(72) Inventors: Ryan Packer, Provo, UT (US); Brian D. Jensen, Provo, UT (US); Anton E. Bowden, Provo, UT (US)

(73) Assignee: Brigham Young University, Provo, UT (US)

( * ) Notice: Subject to any disclaimer, the term of this patent is extended or adjusted under 35 U.S.C. 154(b) by 217 days.

(21) Appl. No.: 18/676,440

(22) Filed: May 28, 2024

(65) Prior Publication Data

US 2024/0423786 A1 Dec. 26, 2024

Related U.S. Application Data

(63) Continuation of application No. 17/242,198, filed on Apr. 27, 2021, now abandoned, which is a continuation of application No. 16/249,844, filed on Jan. 16, 2019, now abandoned.

(60) Provisional application No. 62/617,725, filed on Jan. 16, 2018.

(51) Int. Cl.

| | |
|---|---|
| ***A61F 2/24*** | (2006.01) |
| ***A61L 27/08*** | (2006.01) |
| ***A61L 27/50*** | (2006.01) |

(52) U.S. Cl.

CPC ............ *A61F 2/2403* (2013.01); *A61L 27/08* (2013.01); *A61L 27/50* (2013.01); *A61F 2230/0069* (2013.01); *A61F 2250/001* (2013.01); *A61L 2400/12* (2013.01)

(58) Field of Classification Search

CPC ............ A61F 2/2403; A61F 2230/0069; A61F 2250/001; A61F 2/2406; A61F 2/2475; A61L 27/08; A61L 27/50; A61L 2400/12; A61L 2430/20

See application file for complete search history.

(56) References Cited

U.S. PATENT DOCUMENTS

| | | | | |
|---|---|---|---|---|
| 6,299,637 B1 * | 10/2001 | Shaolian | A61F 2/2475 623/1.24 | |
| 10,201,425 B2 * | 2/2019 | Ku | A61F 2/2475 | |
| 12,588,987 B2 * | 3/2026 | Hariton | A61F 2/2418 | |
| 2003/0055496 A1 * | 3/2003 | Cai | A61F 2/2412 623/2.19 | |

(Continued)

*Primary Examiner* — Bruce E Snow

(74) *Attorney, Agent, or Firm* — Thorpe North & Western, LLP

(57) ABSTRACT

A prosthetic venous valve device is disclosed and described, having a valve base including a cylindrical shape with a lumen configured for axial blood flow, the valve base further including an anterograde end and a retrograde end, a pair of flexure pivots coupled to opposite sides of the valve base at the anterograde end, and a pair of leaflets opposingly positioned with respect to one another and each pivotally coupled to one of the pair of flexure pivots, the pair of leaflets being separated from one another in a default open position, wherein the pair of leaflets are structurally configured to pivot from the default open position toward one another to close the prosthetic venous valve to limit retrograde venous blood flow under normal physiologic venous conditions.

10 Claims, 6 Drawing Sheets

(56) References Cited

U.S. PATENT DOCUMENTS

2012/0053676 A1* 3/2012 Ku .......................... A61F 2/2475
623/1.26

* cited by examiner

PROSTHETIC VENOUS VALVE DEVICES AND ASSOCIATED METHODS

CROSS-REFERENCE TO RELATED APPLICATIONS

This application is a continuation of U.S. patent application Ser. No. 17/242,198, filed on Apr. 27, 2021, which is a continuation of U.S. patent application Ser. No. 16/249,844, filed on Jan. 16, 2019, which claims the benefit of U.S. Provisional Patent Application No. 62/617,725, filed on Jan. 16, 2018, each of which is incorporated herein by reference in their entirety.

BACKGROUND

Chronic venous disease (CVD) is a very common problem in the medical field. Varicose veins affect more than 25 million adults in the United States, and more than 6 million are affected with advanced venous diseases. Varicose veins occur when veins become dilated and overfilled with blood. They appear purple or red in color and are often painful. Individuals with varicose veins often have symptoms of aching, burning, pressure, heaviness, or weakness in the legs after standing or sitting for a long period of time. Chronic venous insufficiency (CVI) is a condition that affects the venous system of the lower extremities. CVI is characterized by constant venous hypertension, which leads to pain, edema, skin changes, and ulcers in the affected individual. These individuals not only suffer the physical effects of the disease but also endure the psychological ailments caused by undesired color changes and bulging of the skin. In severe cases of CVI involving deep vein thrombosis and pulmonary embolism, death can occur.

Current treatments for CVI treat the symptoms of the disease rather than its source. Generally, doctors will first apply compression therapy, and if needed follow that with laser ablation, sclerotherapy, or stripping. These treatments remove the affected vein from the venous system but do not treat the source of the problem. A properly functioning venous system will return blood to the heart by means of the interaction of a central pump, a pressure gradient, a peripheral venous pump, and competent venous valves. Often the main source of the problem is venous valve dysfunction. The purpose of venous valves is to direct blood back toward the heart and impede reverse flow. In the case of CVI, the valves do not close properly and thus cause hypertension and blood pooling in the lower limbs. When the individual's symptoms become serious enough, the source of the problem can be resolved by performing valve reconstruction surgery. The long-term success of such methods, however, can be low depending on the type of surgery performed, and in some cases the entire venous valve may be destroyed, which makes surgery very challenging or even impossible in some cases.

DESCRIPTION OF EMBODIMENTS

Figure 1:
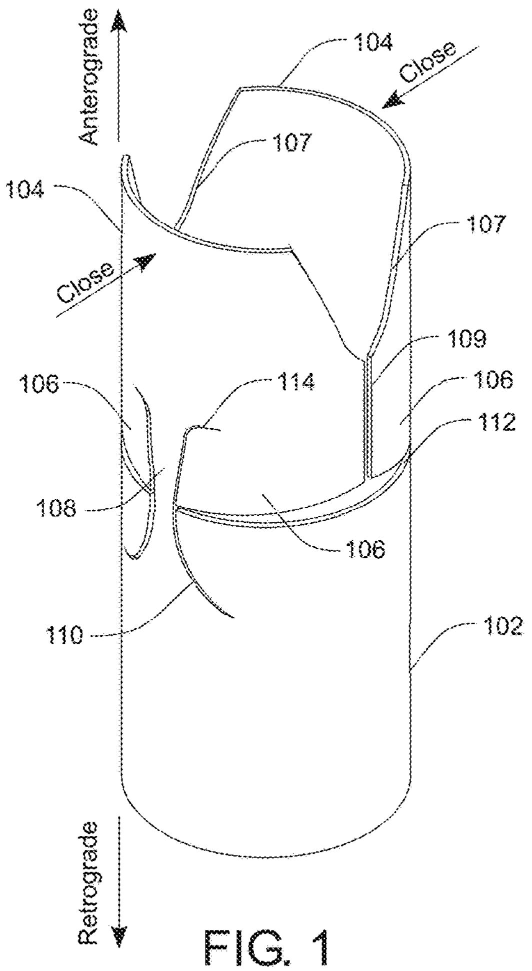
FIG. 1 illustrates a prosthetic venous valve device in accordance with an example embodiment.

Although the following detailed description contains many specifics for the purpose of illustration, a person of ordinary skill in the art will appreciate that many variations and alterations to the following details can be made and are considered included herein. Accordingly, the following embodiments are set forth without any loss of generality to, and without imposing limitations upon, any claims set forth. It is also to be understood that the terminology used herein is for describing particular embodiments only, and is not intended to be limiting. Unless defined otherwise, all technical and scientific terms used herein have the same meaning as commonly understood by one of ordinary skill in the art to which this disclosure belongs. Also, the same reference numerals in appearing in different drawings represent the same element. Numbers provided in flow charts and processes are provided for clarity in illustrating steps and operations and do not necessarily indicate a particular order or sequence.

Furthermore, the described features, structures, or characteristics can be combined in any suitable manner in one or more embodiments. In the following description, numerous specific details are provided, such as examples of layouts, distances, network examples, etc., to provide a thorough understanding of various embodiments. One skilled in the relevant art will recognize, however, that such detailed embodiments do not limit the overall concepts articulated herein but are merely representative thereof. One skilled in the relevant art will also recognize that the technology can be practiced without one or more of the specific details, or with other methods, components, layouts, etc. In other instances, well-known structures, materials, or operations may not be shown or described in detail to avoid obscuring aspects of the disclosure.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term in this written description, like "comprising" or "including," it is understood that direct support should be afforded also to "consisting essentially of" language as well as "consisting of" language as if stated explicitly and vice versa.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a given term, metric, value, range endpoint, or the like. The degree of flexibility for a particular variable can be readily determined by one skilled in the art. However, unless otherwise expressed, the term "about" generally provides flexibility of less than 1%, and in some cases less than 0.01%. It is to be understood that, even when the term "about" is used in the present specification in connection with a specific numerical value, support for the exact numerical value recited apart from the "about" terminology is also provided.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually. This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of phrases including "an example" or "an embodiment" in various places throughout this specification are not necessarily all referring to the same example or embodiment.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," "lower," "upper," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

As used herein, comparative terms such as "increased," "decreased," "better," "worse," "higher," "lower," "enhanced," and the like refer to a property of a device, component, or activity that is measurably different from other devices, components, or activities in a surrounding or adjacent area, in a single device or in multiple comparable devices, in a group or class, in multiple groups or classes, or as compared to the known state of the art. For example, a data region that has an "increased" risk of corruption can refer to a region of a memory device which is more likely to have write errors to it than other regions in the same memory device. A number of factors can cause such increased risk, including location, fabrication process, number of program pulses applied to the region, etc.

An initial overview of embodiments is provided below, and specific embodiments are then described in further detail. This initial summary is intended to aid readers in understanding the disclosure more quickly and is not intended to identify key or essential technological features, nor is it intended to limit the scope of the claimed subject matter.

The primary function of the venous system is to return blood to the heart. Gravity and hydrostatic pressure oppose returning venous flow when an individual is in an upright position. To overcome this deficit, the body uses a system of venous valves and a peripheral pump mechanism (powered by the muscles of the lower limbs) to overcome the forces of gravity. Blood circulates through the arteries due to dynamic pressure that originates from the heart. However, the majority of this dynamic pressure is dissipated by the capillaries. Hydrostatic pressure in the veins is produced by the weight of the blood column below the right atrium. Venous return from the lower extremities is achieved by pushing blood with the lower extremity muscle pumps, while the venous valves prevent retrograde flow of the blood moving downward.

The main cause of chronic venous insufficiency (CVI) results from venous valves becoming incompetent and thus failing to seal properly, resulting in venous reflux and distal venous hypertension. Currently there are few options for fixing incompetent or failed venous valves. In some cases, the valve can be reconstructed surgically, a process known as valvuloplasty, which has about a 70% success rate. If the valve cannot be repaired, valve transplants from other parts of the patient's venous system can be performed, but this procedure is successful less than 50% of the time.

One potential solution to treat the underlying source of CVI is an implantable prosthetic venous valve that would restore proper function of the damaged venous valve. Many attempts have been made to make such a prosthetic venous valve, but none have been sufficiently successful for use in the medical field. Some of the primary problems with previous prosthetic venous valves include their competency, patency, thrombogenicity, biocompatibility, and issues related to incorrect sizing.

Prosthetic venous valves can generally be categorized into two groups: bioprosthetic and mechanical valves. Bioprosthetic valves are valves made of organic material from other animals or humans. Mechanical valves are created from man-made materials. In some cases, bioprosthetic valves have been designed using tissue derived from human umbilical veins, allografts of valves from animals such as dogs or sheep, or a combination of metal stents and valves from dogs or cows. Unfortunately, tests using these valves have shown them to have significant inflammatory responses, leading to generally poor performance in animal tests.

Extensive research has also been done on mechanical venous valves. In some cases, such valves have been constructed from platinum or pyrolytic carbon-covered titanium, polyether urethane, and poly(vinyl-alcohol) (PVA) cryogel. Work with these valves has shown that the three main causes for valve failure are biomaterial-induced thrombosis, very high shear stress rate platelet activation and aggregation, and very low shear stress rate coagulation. Although progress has been made using mechanical venous valves, no valve is yet commercially available for implantation due at least to these aforementioned problems.

The primary problems that have thus prevented the medical acceptance and use of prosthetic venous valves include their biocompatibility, thrombogenicity, correct sizing, and durability. A prosthetic venous valve design that overcomes these problems should have certain characteristics that are similar to a native venous valve. Regarding leaflet operation, naturally closed leaflets should open at a physiologically appropriate hydrostatic pressure such as, for example, 5 mmHg. Naturally open leaflets should close at a physiologically appropriate hydrostatic pressure such as, for example, 20 mmHg. Additionally, the opening and closing of the leaflets should be accomplished without exceeding the ultimate strength of the leaflet material. As another example, a prosthetic venous valve should be constructed of a biocompatible material that does not cause a foreign body reaction and is resistant to cell buildup on the valve structure. In yet another example, a prosthetic venous valve should be antithrombogenic. Coagulation can occur above the maximum physiological venous wall shear rate of 3,500 $s^{-1}$. Additionally, blood stagnation can occur below the minimum physiological venous wall shear rate of 46 $s^{-1}$. To avoid thrombus formation, a prosthetic venous valve design should thus have shear rates above 46 $s^{-1}$ and below 3,500 $s^{-1}$.

The presently disclosed technology overcomes these problems though a novel prosthetic venous valve design that is biocompatible and that minimizes thrombus formation and growth. Such a prosthetic venous valve can thus be utilized to treat secondary venous incompetence for patients with CVI or to prevent CVI from developing. The prosthetic venous valve can be made from a biocompatible material such as, for example, infiltrated carbon nanotubes (I-CNTs), and can be structurally designed and configured to function in a similar manner to a native venous valve. As one example, thrombus formation can be minimized by utilizing a prosthetic venous valve geometry that reduces the wall shear rates in the vein, which have been shown to correlate to thrombus growth. The present prosthetic venous valve has shear rates that are well within the range between 46 $s^{-1}$ and 3,500 $s^{-1}$. In some examples, the prosthetic venous valve can have a maximum shear rate of less than or equal to about 2,100 $s^{-1}$ for anterograde venous blood flow. In other examples, the prosthetic venous valve can have a maximum shear rate of less than or equal to about 1,100 $s^{-1}$ for anterograde venous blood flow. In yet another example, the prosthetic venous valve can have a maximum shear rate of less than or equal to about 300 $s^{-1}$ for anterograde venous blood flow. Furthermore, the prosthetic venous valve implanted into a vein can thus induce valve leaflet operation under normal venous conditions in a similar manner to a native venous valve without material or structural failure. As such, the presently disclosed prosthetic venous valve can direct venous blood to the heart and reduce venous hypertension that results from reflux of blood to the lower extremities. Such will allow the body to heal more effectively and the function of the venous system can be restored.

The present prosthetic venous valve can be configured to have a default open state or a default closed state. For the default open state, the prosthetic venous valve closes under normal physiologic venous conditions. For example, at a retrograde hydrostatic pressure of from about 15 mmHg to about 25 mmHg at the anterograde end, a prosthetic venous valve in an open state, including a default open state configuration, will close. As another example, at a retrograde hydrostatic pressure of about 20 mmHg at the anterograde end, a prosthetic venous valve in an open state, including a default open state configuration, will close. As a further example, at an anterograde hydrostatic pressure of less than or equal to about 5 mmHg at the retrograde end, a prosthetic venous valve in a closed state, including a default closed state configuration, will open. As another example, at an anterograde hydrostatic pressure of from about 0.001 mmHg to about 5.00 mmHg at the retrograde end, a prosthetic venous valve in a closed state, including a default closed state configuration, will open. As yet another example, at an anterograde hydrostatic pressure of about 5 mmHg at the retrograde end, a prosthetic venous valve in a closed state, including a default closed state configuration, will open. It is additionally noted that the prosthetic venous valve can be sufficiently structurally similar to the native venous valve so as to not significantly interfere with the fluid dynamics of the vein.

The present disclosure provides prosthetic venous valves that mimic the opening and closing dynamics of natural venous valves and greatly reduce thrombogenic issues through low wall shear rates and the minimization of regions of stagnant blood. The prosthetic venous valve is additionally made using a material or materials that do not promote thrombus formation. It is generally noted that the present prosthetic venous valve design can be used in a variety of locations and is not limited to the examples described herein.

One example of a prosthetic venous valve is shown in FIG. 1, which can include a valve base 102 and a pair of opposingly positioned leaflets 104. In example shown in FIG. 1, the pair of leaflets 104 are shown opposingly disposed and shaped as a divided cylindrical sidewall that extends linearly from the anterograde end of the valve base 102 (i.e., the cylindrical sidewall of the valve base 102). In other words, the example of FIG. 1 shows a portion of the valve base 102 that has been divided at dividing line 109 linearly to form the pair of leaflets 104. Due to the linear division, the pair of leaflets 104 are colinear along the dividing line 109 that formed them. The valve base 102 can have a cylindrical shape with a lumen configured for axial blood flow. Anterograde and retrograde axial blood flow directions are indicated by the arrows at each end of the prosthetic venous valve. Additionally, the anterograde arrow signifies the anterograde end of the prosthetic venous valve and the retrograde arrow signifies the retrograde end of the prosthetic venous valve. Similarly, the anterograde end of the valve base 102 is opposite to the retrograde end of the valve base 102 and is shown as the anterograde edge 112. It is noted that the example shown in FIG. 1 is in the default open state with the leaflets 104 positioned apart from one another, which are aligned with the cylindrical shape of the valve base when in this default open position. The example of FIG. 1 additionally shows a taper 107 extending from each dividing line.

Each leaflet 104 can be pivotally coupled to the valve base 102 by a leaflet connection segment, also described as a flexural pivot 108. The prosthetic venous valve is shown in an open position in FIG. 1, with the leaflets 104 positioned away from one another. This open position can include, as described above, a prosthetic venous valve configured to have a default open state, as well as an open position of a prosthetic venous valve configured to have a default closed state. When the prosthetic venous valve closes, the leaflets 104 move toward one another in a general direction indicated by the arrows labeled “close.” The closure of the leaflets 104 blocks at least a portion of the anterograde end of the valve base 102, thus blocking at least a portion, if not all, of the retrograde blood flow when in use. Additionally, each leaflet 104 can include a pair of leaflet flaps 106 extending downward from opposite lower sides of the leaflet 104 on either side of the flexural pivot 108. The leaflet flaps 106 can function to further block retrograde blood flow when the prosthetic venous valve is closing or in the closed state.

The flexural pivot 108 can be formed from a portion of the valve base 102, as shown in FIG. 1, or the flexural pivot can be formed separately from the valve base and coupled thereto (not shown). While flexural pivot can begin at, or attach to, the anterograde edge 112, the flexural pivot 108 shown in the example of FIG. 1 extends from within the valve base 102 below the anterograde edge 112. In this case, the portion of the flexural pivot 108 located within the valve base 102 is defined by flexural pivot cuts 110. These flexural pivot cuts 110 can extend upwardly to the bottom edge of the leaflets 104. In this example, an upper portion of the flexural pivot cuts 110 can extend around a portion of the circumference at the bottom edge of the leaflets 104 and is referred to herein as the circumferential flexural pivot cut 114. In the example shown in FIG. 1, the portion of the flexural pivot cuts 110 above the anterograde edge 112 of the valve base defines one edge of each leaflet flap 106. In the example shown in FIG. 1, a pair of the flexural pivot cuts 110 flare away from on another at their retrograde end and their anterograde end 114. The circumference around the bottom edge of the leaflets 104 at the circumference flexural pivot cuts 114 similarly defines the boundary between the leaflets 104 and the leaflet flaps 106.

In one example the leaflets 104 and the leaflet flaps 106 are coupled to the valve base 102 solely through the flexural pivots 108. This arrangement allows the pivot flexibility of the leaflets 104 to be adjusted relative to the valve base 102 through alteration of the physical configuration and/or positioning of the flexural pivot 108. In some cases, such can include altering the thickness of the flexural pivot or a portion of the flexural pivot. In other cases, the size and/or shape of the flexural pivot 108 can be altered to affect leaflet flexibility. For example, the width of the flexural pivot 108 can be varied at the apex, the base, and/or at any point therebetween. Altering the width of the flexural pivot 108 can involve increasing or decreasing the distance between the flexural pivot cuts 110, altering the shapes of the flexural pivot cuts 110, and the like. The bottom edge of the flexural pivot cuts 110 in the valve base 102 can be varied in a circumferential direction to increase or decrease the area of material coupling the valve base 102 to the flexural pivot 108, which can also affect the flexibility provided by the flexural pivot 108. Similarly, the circumferential flexural pivot cuts 114 can be varied in a circumferential direction to increase or decrease the area of material coupling the leaflets 104 to the leaflet flaps 106. Such variation can affect the flexibility of the leaflets 104 relative to the leaflet flaps 106. In yet other cases, the position of the flexural pivot 108 relative to the valve base 102, as well as the extent and positioning of the coupling therebetween, can be altered to affect leaflet flexibility. For example, further variation can be achieved by altering the distance between the anterograde edge 112 of the valve base 102 and the points where the flexural pivot cuts 110 begin, by varying the distance from the bottom edges of the leaflet flaps 106 and the circumferential flexural pivot cuts 114, and the like.

The leaflet flexibility thus affects the behavior of the leaflets 104 relative to one another when under fluid pressure, which is thus a factor affecting the opening and closing dynamics of the prosthetic venous valve. Other features that affect leaflet flexibility, either in the leaflets themselves or in the flexural pivot, can also be included that can affect the overall functionality of the prosthetic venous valve in a fluid environment. Any such feature is thus considered to be within the present scope.

The prosthetic venous valve can have various physical dimensions, which can vary depending on the location into which the prosthetic venous valve will be implanted, the physical characteristics of individual patients, and the like. In one example, the intended location for implantation of a prosthetic venous valve is in the common femoral vein where a majority of venous valve problems occur. In this case, the common femoral vein has an average inside diameter of about 12 mm, which can provide the appropriate diameter sizing for prosthetic venous valve design. In some examples, the length of the prosthetic venous valve can be sufficiently long to provide stability, but not so long as to interfere with the fluid dynamics of the vein. In one example, the length of the prosthetic venous valve can be between 24 mm and 48 mm. Native vein valves tend to be about twice as long as the diameter of the vein. The length of the valve base, for example, can be sufficiently long to allow secure attachment in the vein and to support the leaflets for proper function. In one non-limiting example, the valve base can be from about 12 mm to about 24 mm long with a valve leaflet length of about 15 mm to about 25 mm long. The thickness of the valve base and leaflet walls can be as thin as possible while still allowing proper support and function of the prosthetic venous valve. In one example, these thicknesses can range from about 0.18 mm to about 0.32 mm, or in another example about 0.27 mm. The flexural pivot can additionally have a wide range of physical characteristics and dimensions depending on the design of the prosthetic venous valve and the desire flexibility of the leaflets. In one non-limiting example, however, the flexure pivot can have an average length of about 8 mm and an average width of about 2.22 mm.

Figure 2:
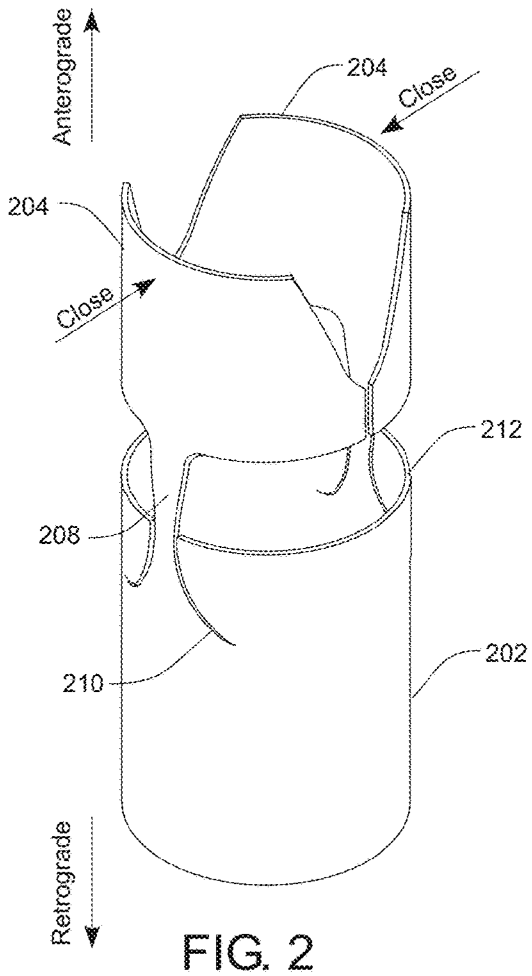
FIG. 2 illustrates a prosthetic venous valve device in accordance with an example embodiment.

FIG. 2 shows another example of a prosthetic venous valve device, which can include a valve base 202 and a pair of opposingly positioned leaflets 204. The valve base 202 can have a cylindrical shape with a lumen configured for axial blood flow. Anterograde and retrograde axial blood flow directions are indicated by the arrows at each end of the prosthetic venous valve. Additionally, the anterograde arrow signifies the anterograde end of the prosthetic venous valve and the retrograde arrow signifies the retrograde end of the prosthetic venous valve. Similarly, the anterograde end of the valve base 202 is opposite to the retrograde end of the valve base 202 and is shown as the anterograde edge 212. It is noted that the example shown in FIG. 2 is in the default open state with the leaflets 204 positioned apart from one another, which are aligned with the cylindrical shape of the valve base when in this default open position.

Each leaflet 204 can be pivotally coupled to the valve base 202 by a flexural pivot 208. The prosthetic venous valve is shown in an open position in FIG. 2, with the leaflets 204 positioned away from one another. This open position can include, as described above, a prosthetic venous valve configured to have a default open state, as well as an open position of a prosthetic venous valve configured to have a default closed state. When the prosthetic venous valve closes, the leaflets 204 move toward one another in a general direction indicated by the arrows labeled “close.” The closure of the leaflets 204 blocks at least a portion of the anterograde end of the valve base 202, thus blocking at least a portion, if not all, of the retrograde blood flow when in use.

The flexural pivot 208 can be formed from a portion of the valve base 202, as shown in FIG. 2, or the flexural pivot can be formed separately from the valve base and coupled thereto (not shown). While flexural pivot can begin at, or attach to, the anterograde edge 212, the flexural pivot 208 shown in the example of FIG. 2 extends from within the valve base 202 below the anterograde edge 212. In this case, the portion of the flexural pivot 208 located within the valve base 202 is defined by flexural pivot cuts 210. These flexural pivot cuts 210 can extend upwardly to the anterograde edge 212. In this example, the flexural pivot 208 extends upwardly past the anterograde edge 212 to couple with the associated leaflet 204.

In one example the leaflets 204 are coupled to the valve base 202 solely through the flexural pivots 208. As described in the example of FIG. 1, this arrangement allows the pivot flexibility of the leaflets 204 to be adjusted relative to the valve base 202 through alteration of the physical configuration and/or positioning of the flexural pivot 208. In some cases, such can include altering the thickness of the flexural pivot or a portion of the flexural pivot. In other cases, the size and/or shape of the flexural pivot 208 can be altered to affect leaflet flexibility. For example, the width of the flexural pivot 208 can be varied at the apex, the base, and/or at any point therebetween. Altering the width of the flexural pivot 208 can involve increasing or decreasing the distance between the flexural pivot cuts 210, altering the shapes of the flexural pivot cuts 210, and the like. The bottom edge of the flexural pivot cuts 210 in the valve base 202 can be varied in a circumferential direction to increase or decrease the area of material coupling the valve base 202 to the flexural pivot 208, which can also affect the flexibility provided by the flexural pivot 208. In yet other cases, the position of the flexural pivot 208 relative to the valve base 202, as well as the extent and positioning of the coupling therebetween, can be altered to affect leaflet flexibility. For example, further variation can be achieved by altering the distance between the anterograde edge 212 of the valve base 202 and the points where the flexural pivot cuts 210 begin.

As has been described, the prosthetic venous valve is designed to open, close, and limit retrograde blood flow in a manner similar to that of a native venous valve. It is noted that some retrograde blood flow is normal in healthy individuals, and thus is part of normal venous valve operation. During native venous valve closure, for example, there is a cessation of anterograde blood flow followed by a brief interval of retrograde blood flow. Generally, retrograde blood flow that lasts less than 0.5 seconds in the upright position is considered healthy, while retrograde blood flow that lasts longer than 0.5 seconds is considered pathologic reflux.

Regarding native venous valve function, such is believed to occur according to four phases. The first phase is the opening phase, where the native leaflets move from a closed position at the center of the vein toward the sinus wall. On average this stage lasts for about 0.3 seconds when the individual is in a horizontal position. The second phase is the equilibrium phase, where the leading edges of the native leaflets remain suspended in the flowing stream and undergo self-excited oscillation, which resembles the motion of a waving flag. The third phase is the closing phase. As the axial velocity of blood passing through the valve decreases, the pressure on the luminal side of the native leaflet decreases. The native leaflets then start moving toward the center of the vein as the pressure on the mural side increases and the pressure on the luminal side decreases. This action generally takes about 0.4 seconds for an individual at rest and is somewhat shorter when foot movements are being performed. The fourth phase is the closed phase, in which the native leaflets are maintained against one another in a closed position. The prosthetic venous valve of the present disclosure has been designed to thus imitate these phases of the native venous valve under normal physiologic conditions.

The prosthetic venous valves according to the present disclosure can be made from any biocompatible material that is capable of being formed into an appropriate valve structure having the physical and geometric characteristics of a native venous valve. In one example, the biocompatible material can be an infiltrated CNT material. In some cases, the CNT material can be disposed on an underlying substrate. Such an underlying substrate can be a temporary support that is fully removed from the finished prosthetic venous valve in some cases, or at least a portion of the underlying support can remain as part of the finished prosthetic venous valve in other cases. As will be recognized in the art, there are a variety of techniques to manufacture CNTs, such as arc discharge, laser ablation, plasma torch, and chemical vapor deposition (CVD), to name a few. The present scope is not limited by the technique of making or preparing CNTs, or by the particular technique of infiltration of the resulting CNTs. In one non-limiting example using MEMS manufacturing processes, however, a mask can be made with a detailed 2-dimensional geometry that matches the desired 2-D geometry of a prosthetic venous valve. The CNTs can be subsequently grown vertically, thus extruding the 2-dimensional geometry defined by the mask into a 3-dimensional pattern of CNTs. Thus, in one aspect, the CNT pattern making up the body of the prosthetic venous valve can be grown from a support substrate, either by this or another technology, with or without using a mask. In another aspect, the CNTs can be grown or otherwise produced on a separate substrate, removed, and subsequently deposited on the support substrate in a molded fashion to form the pattern of CNTs.

The CNTs formed or otherwise deposited on the support substrate can then be infiltrated by an infiltrant material to bind the CNTs together into a CNT layer. As the CNT pattern prior to infiltration corresponds to the desired structure and geometry of a prosthetic venous valve, the resulting CNT layer has the desired structure and geometry of the prosthetic venous valve. Any material capable of being used to infiltrate CNTs that is also biocompatible over the long term can be used as an infiltrant material. Various infiltrant materials can be utilized, including, without limitation, carbon, pyrolytic carbon, carbon graphite, various polymers, and combinations thereof.

The support substrate for growing the CNT layer can have a variety of configurations. In one example, the support substrate can be a rod or tube having an outside diameter to provide a desired inside diameter of the resulting prosthetic venous valve. In another example, the outside diameter of the rod or tube can have an outside diameter that is greater than the desired inside diameter of the resulting prosthetic venous valve, where the excess of material can be utilized in an overlapping fashion to create a size adjustment seam. CNTs can be deposited onto the outside of the support rod or tube in a pattern and thickness to create the structures that make up the prosthetic venous valve having an appropriate wall thickness. Following infiltration of the CNT pattern to form a self-supporting CNT layer, the support rod or tube can be removed from the CNT layer, resulting in a prosthetic venous valve.

In another example, the support substrate can be a planar substrate upon which a planar 2-D pattern is outlined. In some cases, a mask can be applied to the planar substrate, where the planar 2-D pattern includes unmasked portions of the planar substrate. CNTs can be grown or otherwise deposited according to the 2-D pattern and extruded to a 3-D pattern of CNTs. Depending on the physical properties of the mask, the CNTs can be grown exclusively in the unmasked portions on the planar substrate or the CNTs can be grown across the mask and the unmasked portions on the planar substrate, where the CNTs on the mask are removed with the mask expose the 3-D pattern of CNTs. It is noted that the 3-D reference to the pattern of CNTs on the planar substrate refers to the thickness of the layer of CNTs extending therefrom. The pattern of CNTs can then be infiltrated with an infiltrant material to form a self-supporting CNT layer. The CNT layer can then be rolled or otherwise formed into its desired cylindrical shape, either with the planar support still attached or following removal of the planar support. The axial seam can then be fixed together at a desired diameter or the axial seam can be formed into an adjustment seam to allow size adjustment to a desired diameter prior to implantation of the prosthetic venous valve. In some examples, the axial seam can be positioned along the valve base at a location that does not extend through either of the pair of leaflets. In cases where it remains coupled to the CNT layer during forming of the cylindrical shape, the planar substrate can subsequently be removed.

In another example, a support substrate that is either in a cylindrical or a planar configuration can have CNTs deposited or formed thereon in a continuous layer without a pattern. Either prior to or following infiltration to form a self-supporting CNT layer, regions of the CNT material can be ablated, etched, or otherwise removed to form the appropriate CNT pattern.

It is generally intended that, in the various examples described above, the support rod or tube be fully removed from the CNT layer to avoid biocompatibility issues arising from any support rod or tube material remaining in the prosthetic venous valve. It is to be understood that in some situations a portion of the support material may remain in the finished prosthetic venous valve device, provided the amount is sufficiently small to avoid biocompatibility issues over the long-term use of the device.

EXAMPLES

The following examples pertain to specific embodiments and point out specific features, elements, or steps that can be used or otherwise combined in achieving such embodiments.

Prosthetic Venous Valve Modeling:

Design Environment

The geometric designing of the prosthetic venous valve was done in Siemens NX 10.0. The NX files were then uploaded to ANSYS for structural analysis. Only half of the valve was modeled due to symmetry and to decrease the computational time in the structural analysis. The venous valve shape was modeled as a thin sheet in NX. The element used in ANSYS was SHELL181, which best represented the valve since its thickness was very small compared to its length. The thickness of the valve was specified in ANSYS. Prior experiments show a Young's modulus and ultimate strength for carbon infiltrated CNT (CI-CNT) of 10 GPa and 153 MPa, respectively. The valve was meshed in ANSYS using 30 element divisions for each line of the model. Displacement constraints were set on the model so that the valve walls did not move. Finally, a pressure was applied to the leaflets of the valve, which represented the hydrostatic or dynamic pressure of blood in the body, depending on whether the model was being tested for opening or closing.

Valve Design

For the prosthetic venous valve design, the manufacturing and hemodynamics were taken into consideration. CNTs are primarily grown on flat surfaces, with some experimental studies done on cylindrical surfaces made of stainless steel. To make growth and manufacturing easier the device can be made on a cylindrical steel rod. The diameter of the prosthetic venous valve was chosen as 12.7 mm, since the closest steel rod dimensions to the common femoral vein is a 0.5-inch diameter rod. The basic design, comprises a cylindrical section that would be fixed in the vein (the valve base with valve leaflets connected to the cylindrical section by short flexible segments (the flexure pivots). To reduce backflow around the flexible segments, flaps were inserted in the design to decrease the amount of open space that blood might pass through (leaflet flaps). The design was optimized to allow the valve to fully close with a hydrostatic pressure of 20 mmHg, with stresses lower than the material's ultimate strength. This objective was achieved using a flexible segment width of 2.22 mm and a flexible segment length of 8 mm. The leaflet length was 20 mm. The valve thickness was 0.27 mm, which is commonly achieved for CNT growth. The CI-CNT prosthetic venous valve produced a deflection of 6.85 mm and had a maximum von Mises stress of 117.17

Figure 3:
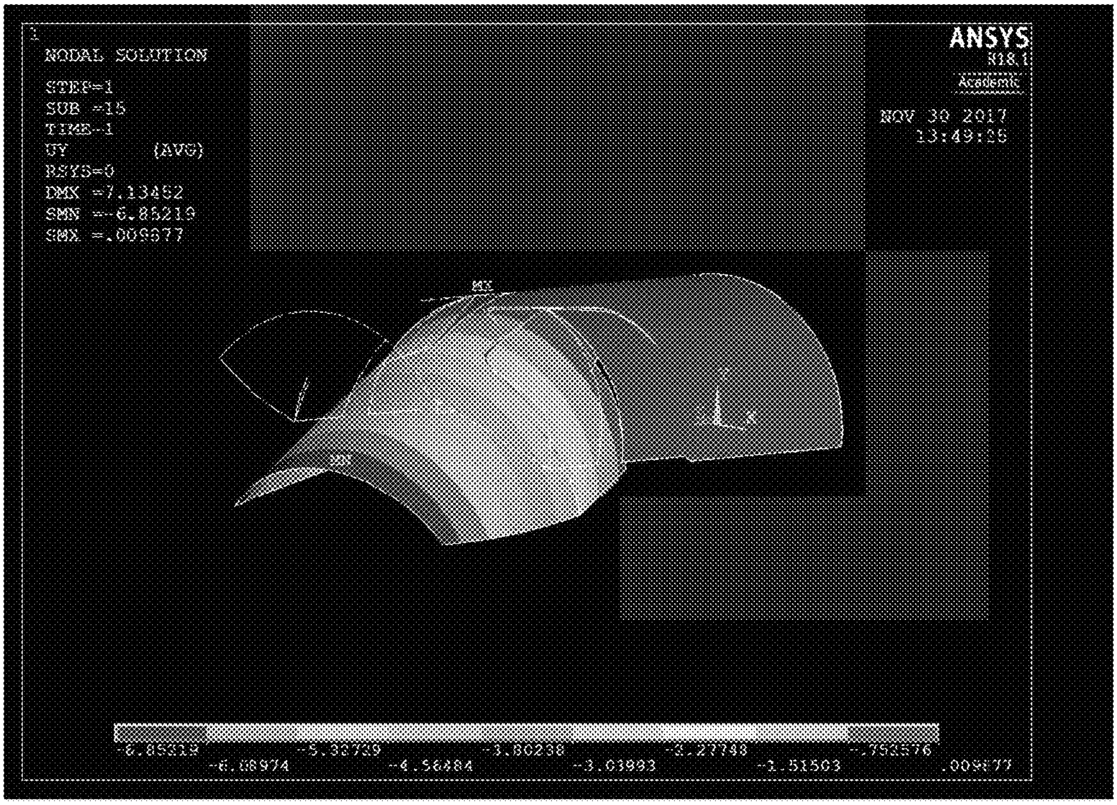
FIG. 3 illustrates modeling data of deflection results in accordance with an example embodiment.
Figure 4:
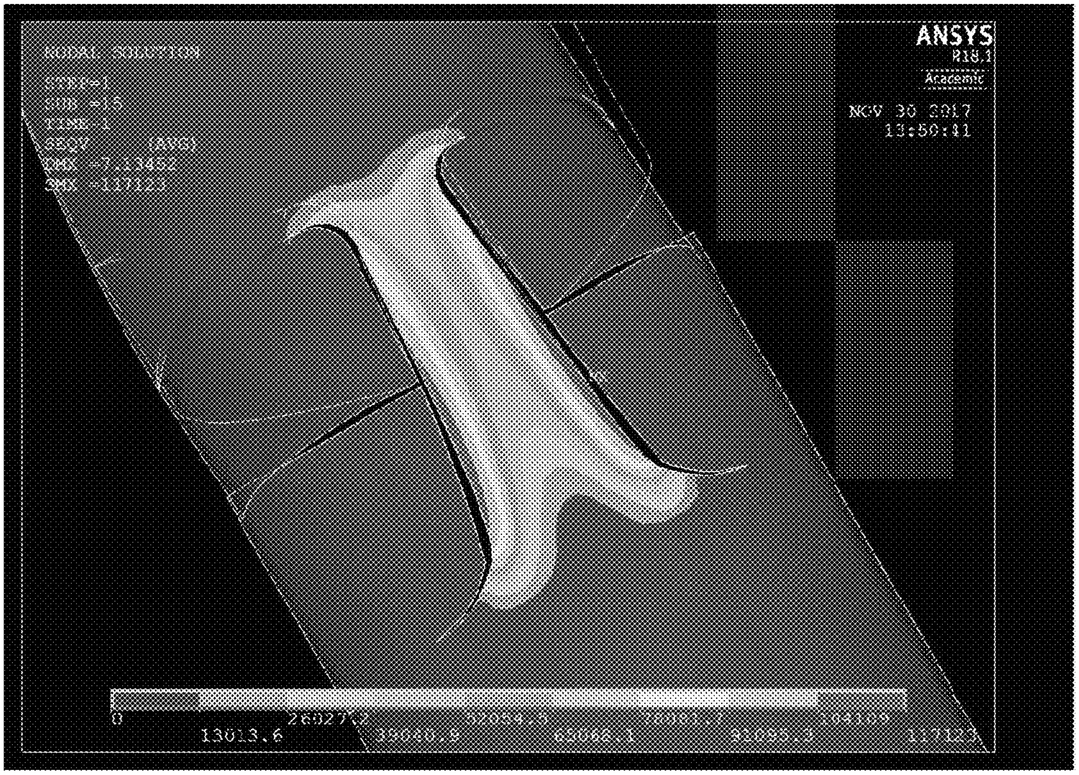
FIG. 4 illustrates modeling data of stress results in accordance with an example embodiment.

MPa (see FIGS. 3 and 4). 6.85 mm of deflection allows the leaflets to move just past the midpoint of the vein and completely seal. The deflection is possible since the maximum von Mises stress is below the ultimate strength of CI-CNTs.

Model Reliability

In the real world the mechanical properties of materials can vary greatly even if the material samples are manufactured with the same conditions and tolerances. This is especially true for the manufacturing of CI-CNTs since the creation process is complex. The manufacturing of CI-CNTs involves depositing several thin films on the surface of the substrate and growing the nanotubes in a furnace with flowing gases. This multi-step process can result in different mechanical properties of the CI-CNTs if the film thicknesses, time in the furnace, or flow of the gases are different between production runs. It is important to design for the mechanical variability of CI-CNTs to ensure the venous valve will function properly despite differences between each manufactured sample.

To test for this scenario the final design was analyzed subsequently with a 20% reduction and a 20% increase in the material's Young's modulus. The deflection decreased to 5.66 mm as the Young's modulus was increased. This change in turn reduced the maximum stress to 114.9 MPa. On the other hand, decreasing the modulus by 20% caused the deflection to increase to 8.67 mm and the maximum stress to increase to 120.69 MPa. This reliability study shows that there is no danger of the prosthetic failing under a variable modulus, but the concern regards the proper sealing of the valve leaflets.

Fluid Dynamic Analysis:

Model Creation

A computational analysis was performed on the prosthetic venous valve design to assess the hemodynamic changes it could create after implantation. The fluent solver in ANSYS Workbench 18.2 was used for the analysis. First the valve design was modeled in AutoCAD 2018 and then uploaded into the Fluid Flow (Fluent) module in the ANSYS Workbench. Since the valve was symmetrical on both sides, only one fourth of the valve was used for the fluid model to reduce the computational time to solve the simulation. The fluid domain was created by filling in the center of the vein with a solid and extracting the solid prosthetic venous valve design. 60 mm of the vein was included after the outlet of the valve to aid in visualizing how the valve would influence exiting flow dynamics. The prosthetic valve was modeled in the open position to determine the maximum velocity and shear rates in the vein. The vein was modeled as 12.7 mm in diameter and 100 mm long.

Initial Conditions

Before the simulation was performed the initial inlet flow condition was obtained. The inlet conditions depend on the material characteristics of blood and the dynamics it has at the inlet of the prosthetic valve. In a worst-case scenario, the highest shear rates would be caused by an inlet flow profile that would drastically change near the vein wall. This scenario would be very similar to a fully developed profile. The peak flow rate in the femoral vein can be up to 1600 mL/min. To determine the distance the flow needs to travel before it becomes fully developed the Reynolds number and viscosity of blood need to be obtained. For Newtonian fluids the viscosity is a linear relationship between the shear stress and shear rate given by Equation I:

$$\tau_{rz}=\mu(\partial v_z)/(\partial r) \quad \text{(I)}$$

Blood can act like either a Newtonian or a non-Newtonian fluid. For shear rates below 50 $s^{-1}$, blood acts like a yield-pseudo plastic fluid and the shear stress is not a linear function of the shear rate. At higher shear rates, above 50 to 80 $s^{-1}$, the viscosity of blood is constant, and the Newtonian equation correctly models its behavior. In larger vessels, the wall shear rate nearly always exceeds 100 s–1, and the average shear rate nearly always exceeds 80 $s^{-1}$. Since the common femoral vein is a deep vein it was assumed that the shear rate would be above 80 $s^{-1}$ and the viscosity of blood would be constant.

The Reynolds number can be calculated by using Equation II:

$$Re=(\rho vD)/\mu \quad \text{(II)}$$

where ρ, v, and μ represent the density, average velocity, and viscosity of blood, respectively, and D represents the diameter of the vein. The density and viscosity of blood at high shear rates are 1056 $kg/m^3$ and 0.00345 Pa·s. The average velocity of blood, v, can be calculated by using the flow rate through the common femoral vein, given by Equation III:

$$v=Q/A \quad \text{(III)}$$

where Q represents the flow rate (1600 mL/min), and A represents the cross sectional area of the vein ($1.27\times10^{-4}$ $m^2$). These equations resulted in an average velocity and Reynolds number of 0.21 m/s and 819.75, respectively.

This shows that the flow through the common femoral vein is laminar. When flow is laminar the entrance length, or distance required for fully developed flow, can be calculated by using Equation IV:

$$L_{entrance}=0.05\,ReD \quad \text{(IV)}$$

This equated to an entrance length of 521 mm. This inlet condition was captured by modeling a 12.7 mm vein that was 600 mm long. Only one fourth of the vein was used due to symmetry and to reduce the computational cost of the problem. The velocity at the entrance of the vein was set at 0.21 m/s and a relative mesh density study was performed until the maximum velocity changed less than 1%. This velocity profile was then saved and used as the inlet profile for modeling the valve.

Meshing

Figure 5:
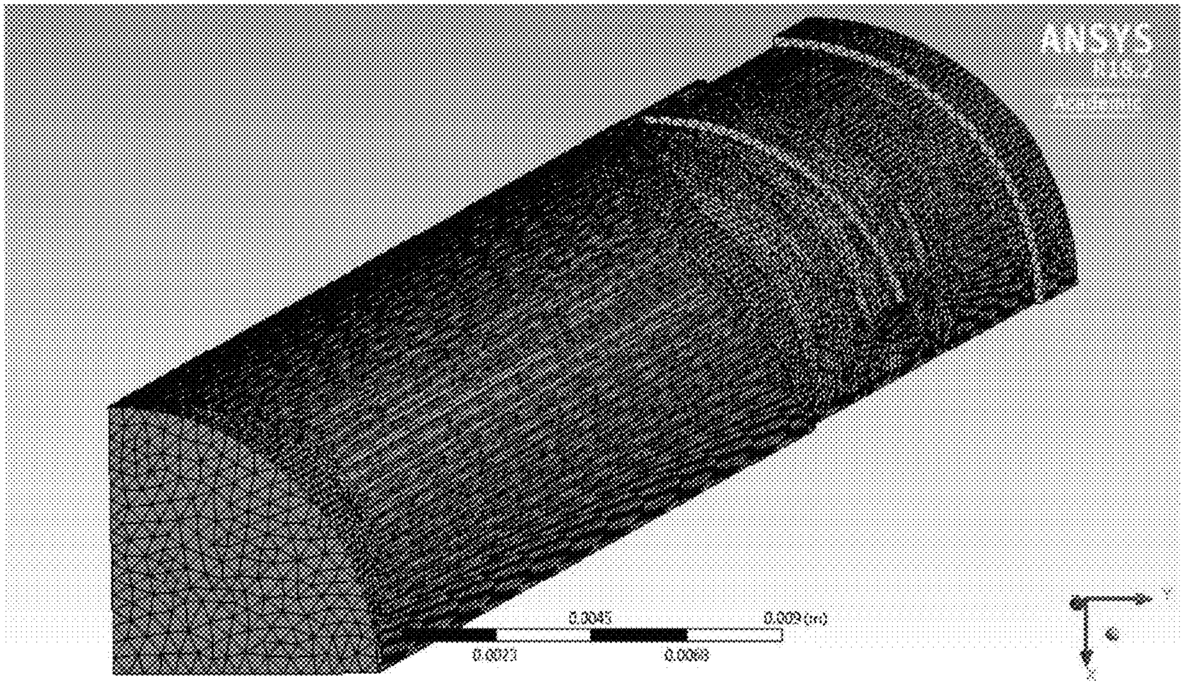
FIG. 5 illustrates modeling data of a mesh of fluid domain in accordance with an example embodiment.

Once the inlet velocity components were saved and the prosthetic venous valve model was uploaded to ANSYS Workbench the fluid domain was meshed. An adaptive medium fine mesh was used with a growth rate of 1.2. A relative mesh density study was performed to determine an acceptable mesh for the fluid analysis. The results are shown in Table 2. The element and defeature sizes were decreased from one test to the next. The defeature size removes small geometric features that are smaller than the specified size. Since the smallest feature in the model had a size of approximately 0.3 mm, the initial defeature size of the mesh was set at 0.3 mm and the initial element size was 1.5 mm. The maximum velocity of the blood was noted after each test of the mesh study to quantify a sufficiently fine mesh. The mesh was considered accurate for the simulation once the maximum velocity of the blood changed less than 1% between the mesh tests. The final mesh size had an element size of 0.375 mm, a defeature size of 0.075 mm, 38,093 nodes, and 181,312 elements. The final mesh is shown in FIG. 5.

TABLE 2

Prosthetic Mesh Study

| Mesh Density | Element Size (mm) | Defeature Size (mm) | Maximum Velocity (m/s) |
|---|---|---|---|
| 1 | 1.5 | 0.3 | .38063 |
| 2 | 0.75 | 0.15 | .38978 |
| 3 | 0.5 | 0.1 | .39588 |
| 4 | 0.375 | 0.075 | .39591 |

CFD Results

Figure 6A:
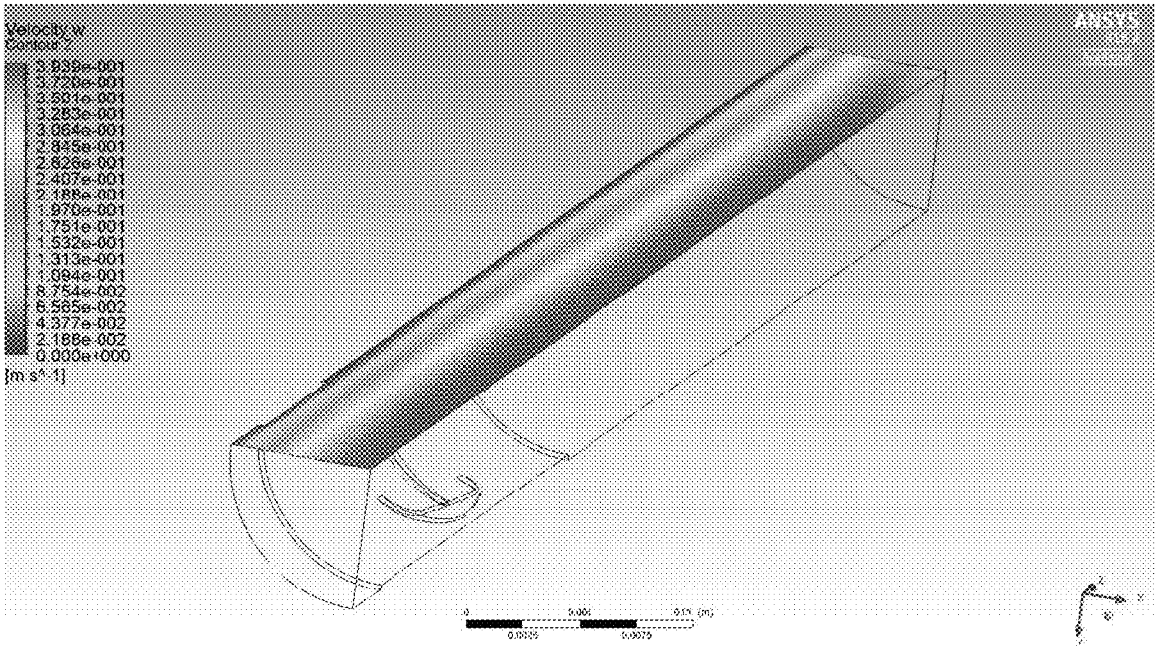
FIG. 6A illustrates modeling data of velocity profiles at the planes of symmetry in accordance with an example embodiment.
Figure 6B:
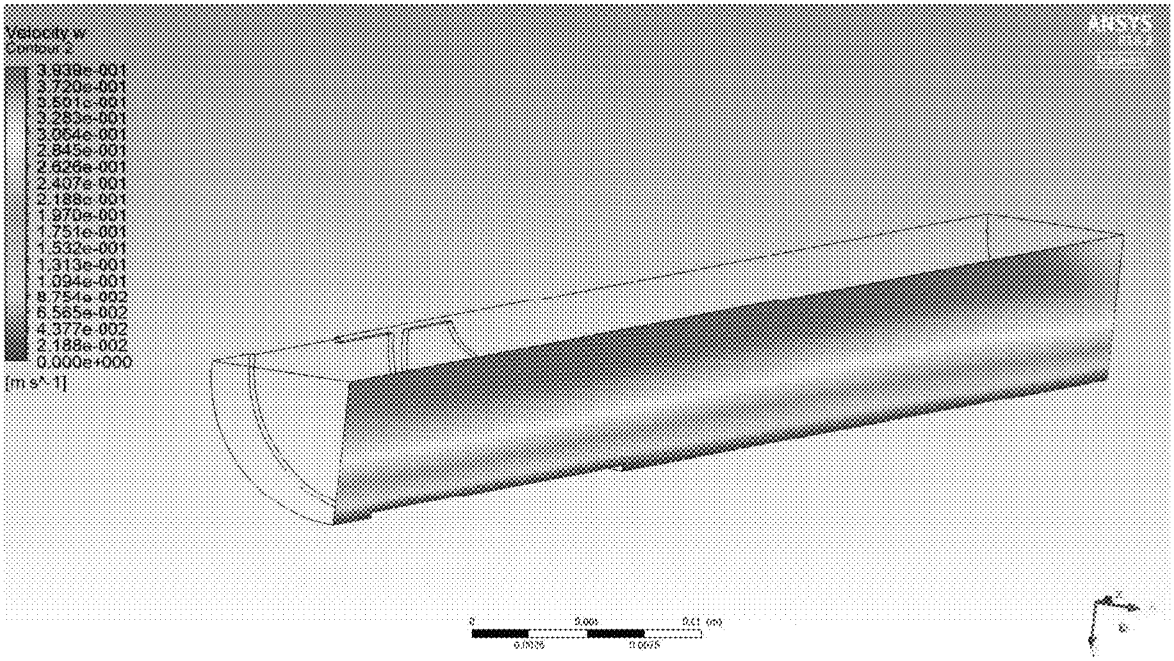
FIG. 6B illustrates modeling data of velocity profiles at the planes of symmetry in accordance with an example embodiment.

The fully developed peak flow rate through the valve resulted in an increase of the maximum velocity from 0.379 m/s to 0.395 m/s at the centerline of the vein (see FIGS. 6A and 6B). The velocity profile throughout the vein was undisturbed with no reversed flow.

Figure 7:
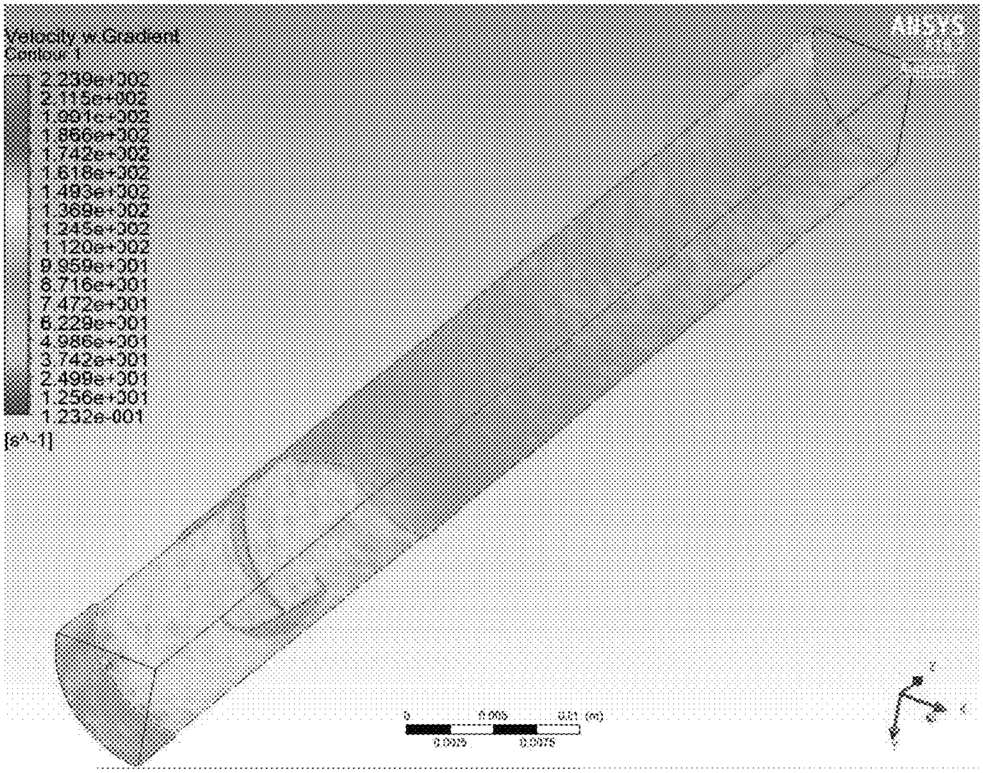
FIG. 7 illustrates modeling data of shear rate throughout the vein in accordance with an example embodiment.
Figure 8:
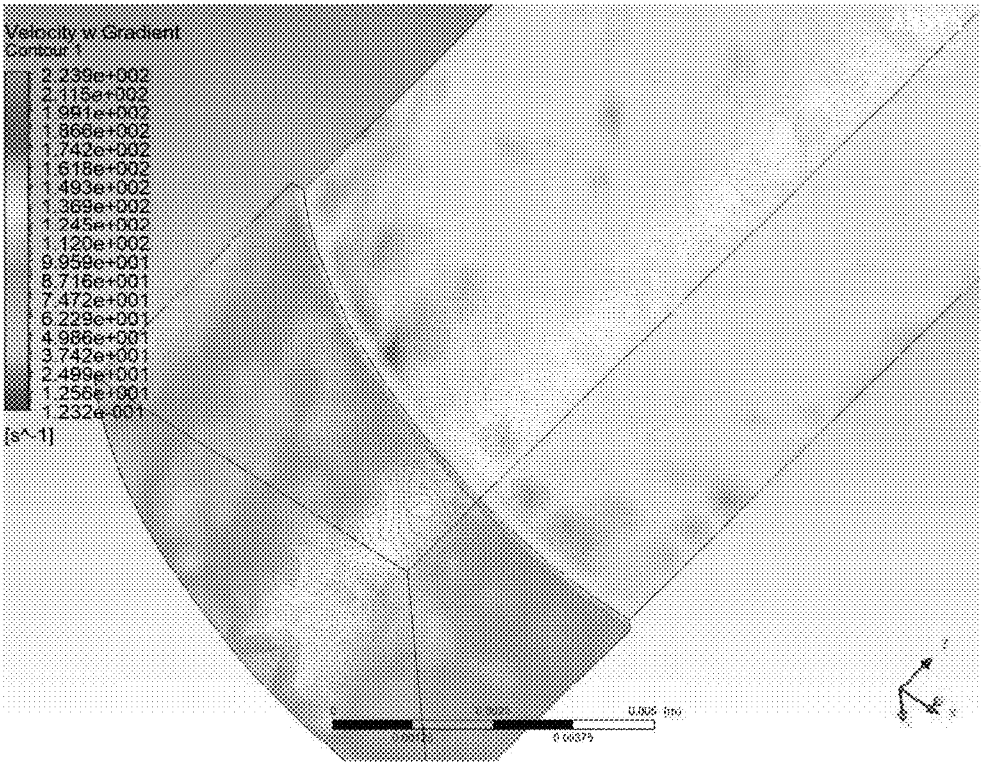
FIG. 8 illustrates modeling data of shear rates near the inlet of the valve in accordance with an example embodiment.

The maximum shear rate in the vein was 225.1 $s^{-1}$. This occurred at the inlet of the venous valve where the inner diameter of the vein decreased due to the valve's thickness (see FIGS. 7 and 8). There was also a smaller region of high shear rates at the corner of the top flap (visible in FIG. 7). Although these shear rates are higher relative to the other shear rates throughout the valve, they are still far below 3500 $s^{-1}$. This indicates that the prosthetic venous valve would be far less likely to form blood clots due to elevated shear rates.

Figure 9:
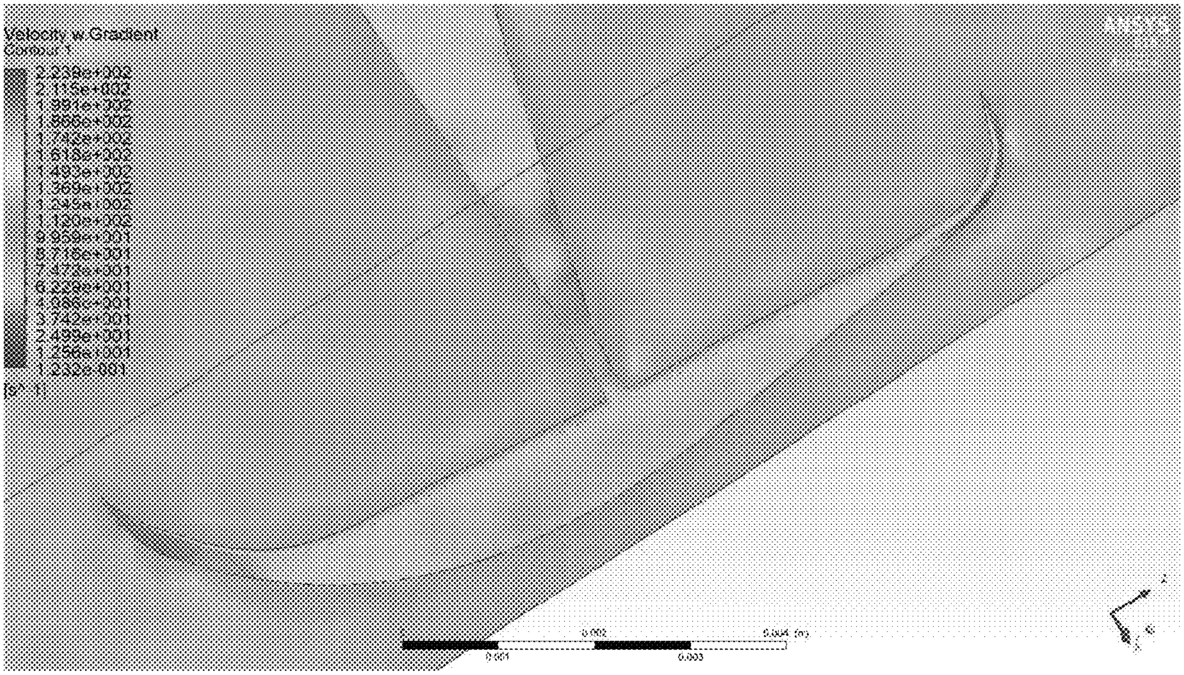
FIG. 9 illustrates modeling data of a region of low shear rates in accordance with an example embodiment.

The minimum shear rate experienced throughout the vein was 0.123 $s^{-1}$. This primarily took place around the borders of the valve leaflets and between the leaflet flaps (see FIG. 9). The lowest shear rates occurred near the top and bottom of the leaflet flaps, which had smaller open areas for blood to pass through. Opening and closing of the valve will help increase the shear rates in these regions. Overall, the average shear rates in the areas around the borders of the leaflets and leaflet flaps were approximately 65 $s^{-1}$. Since the average shear rates in these areas is above 46 $s^{-1}$, thrombosis formation would likely not occur.

Model Validation

To ensure that the CFD shear rate results were correct and in the appropriate range a theoretical wall shear rate in the common femoral vein was calculated. Assuming the blood in the vein is a Newtonian fluid, the flow is steady and laminar, and the vein is straight and inelastic, Poiseuille's law may be applied to determine the wall shear rate, given by Equation V:

$$\gamma = (32Q)/(\pi d^3) \tag{v}$$

where Q is the flow rate through the vein, d is vein diameter, and y represents the wall shear rate. Using the peak flow experienced in the femoral vein, 1600 mL/min, and a vein diameter of 12.7 mm, the wall shear rate would be 132.6 $s^{-1}$. This shows that in a common femoral vein without any obstructions or venous valve the wall shear rate would be close to 132.6 $s^{-1}$. The theoretical shear rate validates the CFD shear rate since the CFD result is slightly above the theoretical value. This slight increase is to be expected due to the inclusion of the prosthetic venous valve.

What is claimed:

1. A prosthetic venous valve, comprising:

a valve base having a cylindrical side wall with a retrograde end and an anterograde end;

a pair of leaflets oppositely disposed and shaped as a divided cylindrical side wall extending linearly from the anterograde end of the cylindrical wall, each of the pair of leaflets being colinear along each dividing line between the pair of leaflets;

a taper extending from each dividing line to an anterograde end on both sides of each leaflet;

a pair of flexural pivots extending linearly from opposite sides of the anterograde end of the cylindrical side wall, such that each flexural pivot of the pair of flexural pivots linearly couples to one leaflet of the pair of leaflets; and pairs of flexural pivot cuts extending along and through the cylindrical side wall from the anterograde end toward the retrograde end to laterally define each of the flexural pivots in the cylindrical side wall, whereby each flexural pivot cut from a pair of flexural pivot cuts flare away from one another at their retrograde end.

2. The prosthetic venous valve of claim 1, wherein the pairs of flexural pivot cuts extend along and through the divided cylindrical side wall of each of the pair of leaflets from the retrograde end toward the anterograde end to laterally define the flexural pivot in each leaflet, whereby each flexural pivot cut from the pair of flexural pivot cuts flare away from one another, thereby defining a leaflet flap on each side of each leaflet.

3. The prosthetic venous valve of claim 2, wherein the pair of leaflets are structurally configured to pivot from a default open position toward one another to close the prosthetic venous valve at a retrograde hydrostatic pressure of from about 15 mmHg to about 25 mmHg at the anterograde end.

4. The prosthetic venous valve of claim 2, wherein the pair of leaflets are structurally configured to pivot from a default open position toward one another to close the prosthetic venous valve at a retrograde hydrostatic pressure of about 20 mmHg at the anterograde end.

5. The prosthetic venous valve of claim 1 having a maximum shear rate of less than or equal to about 2,100 $s^{-1}$ for anterograde venous blood flow.

6. The prosthetic venous valve of claim 1 having a maximum shear rate of less than or equal to about 1,100 $s^{-1}$ for anterograde venous blood flow.

7. The prosthetic venous valve of claim 1 having a maximum shear rate of less than or equal to about 300 $s^{-1}$ for anterograde venous blood flow.

8. The prosthetic venous valve of claim 1, wherein the valve base, the pair of flexural pivots, and the leaflets are made of a biocompatible material.

9. The prosthetic venous valve of claim 8, wherein the biocompatible material is carbon-infiltrated carbon nanotubes (CI-CNTs).

10. The prosthetic venous valve of claim 1, wherein the pair of leaflets are aligned with the cylindrical shape of the valve base when in the default open position.

* * * * *